United States Patent [19]

Petrassevich

[11] 4,337,763

[45] Jul. 6, 1982

[54] ILLUMINATED SURGICAL INSTRUMENT

[75] Inventor: Cornel H. Petrassevich, Philadelphia, Miss.

[73] Assignee: The United States of America as represented by the Department of Health, Education and Welfare, Washington, D.C.

[21] Appl. No.: 141,764

[22] Filed: Apr. 21, 1980

[51] Int. Cl.³ .............................................. A61B 17/24
[52] U.S. Cl. ........................................ 128/20; 128/11
[58] Field of Search ............................ 128/3, 6, 10–20

[56] References Cited

U.S. PATENT DOCUMENTS

| 339,754 | 4/1886 | Yoote | 128/16 |
| 458,708 | 9/1891 | Daily | 128/18 |
| 471,990 | 3/1892 | Daily | 128/18 |
| 648,673 | 5/1900 | Schlesinger | 362/157 |
| 659,182 | 10/1900 | Pilling | 128/20 |
| 872,344 | 12/1907 | Griswold | 128/18 |
| 1,747,407 | 2/1930 | Wappler | 128/6 |
| 1,932,473 | 10/1933 | Morgen et al. | 128/16 |
| 2,224,464 | 12/1940 | Wolf | 128/6 |
| 2,296,793 | 9/1942 | Kirschbaum | 128/20 |
| 2,637,317 | 5/1953 | Martin | 128/6 |
| 3,826,428 | 7/1974 | Gobels | 128/11 |

FOREIGN PATENT DOCUMENTS

| 303141 | 1/1918 | Fed. Rep. of Germany | 128/17 |
| 1912 | of 1913 | United Kingdom | 128/20 |
| 680219 | 1/1952 | United Kingdom | 128/6 |
| 683731 | 3/1952 | United Kingdom | 128/6 |

Primary Examiner—Robert W. Michell
Assistant Examiner—Nancy A. B. Swisher
Attorney, Agent, or Firm—Browdy and Neimark

[57] ABSTRACT

A medical implement and more particularly a surgical retractor or speculum having an improved functional configuration and further provided with means for illuminating the interior of a natural body cavity or a cavity formed by incision or a wound.

4 Claims, 4 Drawing Figures

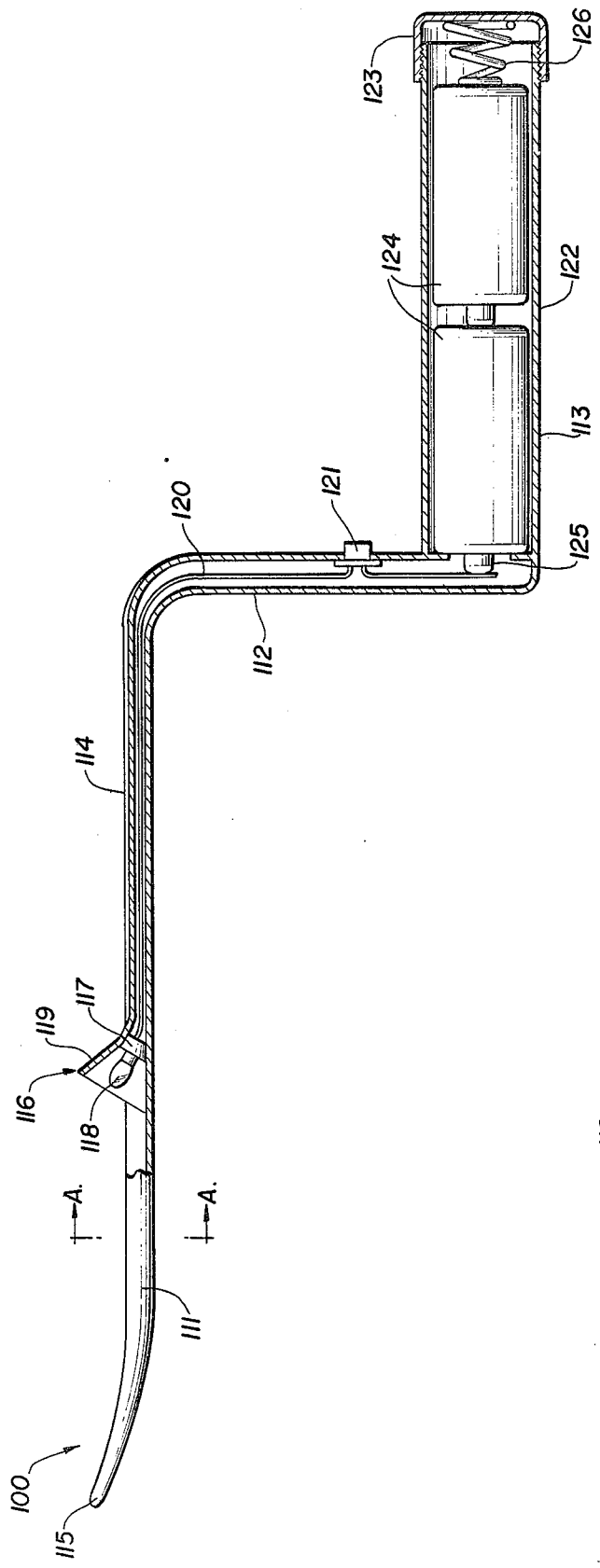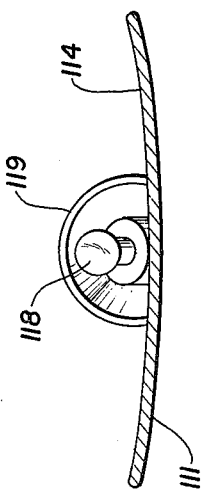

ILLUMINATED SURGICAL INSTRUMENT

FIELD OF INVENTION

The present invention relates to an illuminated retractor or speculum, and more particularly to a surgical retractor or speculum or the like having an improved functional configuration and provided with means for illuminating the interior of a natural body cavity or a cavity formed by incision or a wound.

BACKGROUND OF INVENTION

Retractors and specula are of the more common implements known to the surgical arts and are employed to hold open or enlarge a body cavity, incision, wound, or the like, so as to enable the physician to examine the interior of the cavity and to facilitate the insertion and manipulation of surgical implements therein. Conventional retractors are characterized by having a blade portion formed with a shallow, concave curvature and a handle affixed to the blade portion and generally disposed at a right angle thereto. Specula are characterized by a pair of thin duck bill-like blades, the lower blade being generally formed integrally with a handle and the upper blade being pivotally movable with respect to the fixed lower blade, the pivot point being located adjacent the handle.

The conventional blade and handle arrangement has been found to be disadvantageous as the handle interferes with the insertion of other surgical implements into the cavity, and this is especially true in the instances where the retractor is employed for obstetrical or gynecological purposes, as great care must be taken when manipulating the retractor to avoid contact of the handle with the inner thighs which are easily contused.

In order to adequately illuminate the internal portions of the cavity under examination, it has often been necessary to provide a light source external of the instrument which often either failed to provide sufficient illumination or interfered with the examining physician's ability to obtain a clear, unobstructed view of the cavity interior, as such external light sources were located at the rear of the instrument.

Thus, it is desirable to provide a light source integral with the retractor or speculum to overcome the problems associated with an external light source. One such means is disclosed in U.S. Pat. No. 3,324,850, which, inter alia, provides a light source mounted in the interior portion of the lower blade. This arrangement has, however, proved unsatisfactory. As it is often necessary to remove samples of tissue from the body cavity for laboratory analysis, the lower blade of the speculum is used to collect such samples. Consequently, a light source located in the lower blade becomes obscured by blood and tissue scrapings, thus diminishing and often obliterating illumination at the very time when adequate illumination is particularly needed.

Another illuminating means has been devised and is described in U.S. Pat. No. 2,296,793, wherein a light source is wholly contained within the shell of the blade, the light being directed through a transparent closure at the tip of the blade. This arrangement has, however, proven unsatisfactory, for when the blade is inserted into the cavity the tip will become immersed in blood or tissue, thus diminishing and often completely obliterating the light. Moreover, the blade must be considerably thicker in order to accommodate the light fixture.

Other illuminated specula and retractors are shown in U.S. Pat. Nos. 726,704; 1,003,232; 1,783,602; 3,776,240; 458,708; 872,344; 339,754; 3,826,248; 471,990; 1,932,473; 648,673; and U.K. Pat. No. 25,040 of 1913. Devices of this general type have also been provided in a number of shapes, such as shown in U.S. Pat. No. 659,182.

All of these devices have, however, suffered from one or more defects; and, insofar as is known, none has ever achieved any substantial acceptance by physicians. The reason for such lack of acceptance is that none of these devices has been constructed in such a way as to provide the correct location of the light source so that the light beam therefrom will not be obscured during use of the instrument and so that the angulation of the light path permits maximum illumination of the interior of the cavity.

Providing light to the internal area of the body for surgery is an old and still unresolved problem. Most lighting mechanisms presently available, e.g. over the shoulder lamps, are not very satisfactory. Attempts by others, such as those set forth in the patents mentioned above (also there is a plastic speculum available which has a fiber optic light source on the bottom portion, but which is not effective because it does not direct light to the proper area), have not solved the problem. Many surgical procedures must be performed blindly because there is still no effective way to illuminate the interior of the body cavities.

SUMMARY OF INVENTION

It is, accordingly, an object of the present invention to overcome defects in prior art, such as indicated above.

It is another object to provide improved illumination of body cavities during surgery when using specula and retractors.

It is yet another object of the instant invention to provide improved illuminated surgical instruments, such as vaginal specula and retractors.

It is still another object of the instant invention to provide an improved vaginal speculum having a light source on the inner surface of the upper blade which light source provides a clear, unobstructed, uniformly lit view of the interior of the body cavity and which will not become obscured or dimmed by reason of removing blood and tissue samples from the cavity.

It is a further object of the instant invention to provide a retractor having an improved functional handle configuration and an integral source of illumination, which will not become obscured when the instrument is inserted into a body cavity; and which has a handle substantially parallel to the horizontal plane of the blade, the handle being joined to the blade via a shorter, substantially vertical shank and further providing a light source centrally located on the upper concave surface of the blade.

The above objects are achieved by providing a double-blade speculum or single-blade retractor which, on the interior of the upper blade of the speculum or on the concave surface of the retractor, has a projecting light fixture which points towards the body cavity created by the instrument, e.g. the opening of the two blades of the speculum, such fixture having a flared socket to serve as a shade for the light bulb and to minimize light scattering so as to direct as much light as possible to the interior of the cavity being examined. The shade screens the bulb from the physician's eye, and eliminates distracting glare. Proper location of the bulb on the upper blade is critical, and it is found that the light must be placed in a location between ¼ and 2/5 from the distal tip of the blade and preferably ⅓ of the distance from the blade tip.

In the case of a two-bladed specula, the light source so placed on the inner surface of the upper blade provides a clear unobstructed uniformly lit view of the interior of the body cavity which will not be obscured during removal of blood and tissue from the cavity. Similarly in the case of the single-bladed retractor, such placement of the light source on the upper concave surface of the blade likewise insures continuous illumination of the body cavity without interference.

BRIEF DESCRIPTION OF THE DRAWINGS

For a better understanding of the invention, as well as the above and other objects and the nature and advantages of the instant invention, possible embodiments thereof will now be described with reference to the attached drawings, it being understood that these embodiments are intended as being merely exemplary and in no way limitative.

FIG. 3 is a side elevation view, partly in section, of a retractor according to the invention, and FIG. 4 is a view taken along line A—A of FIG. 3.

DETAILED DESCRIPTION OF EMBODIMENTS

Figures 1, 2:
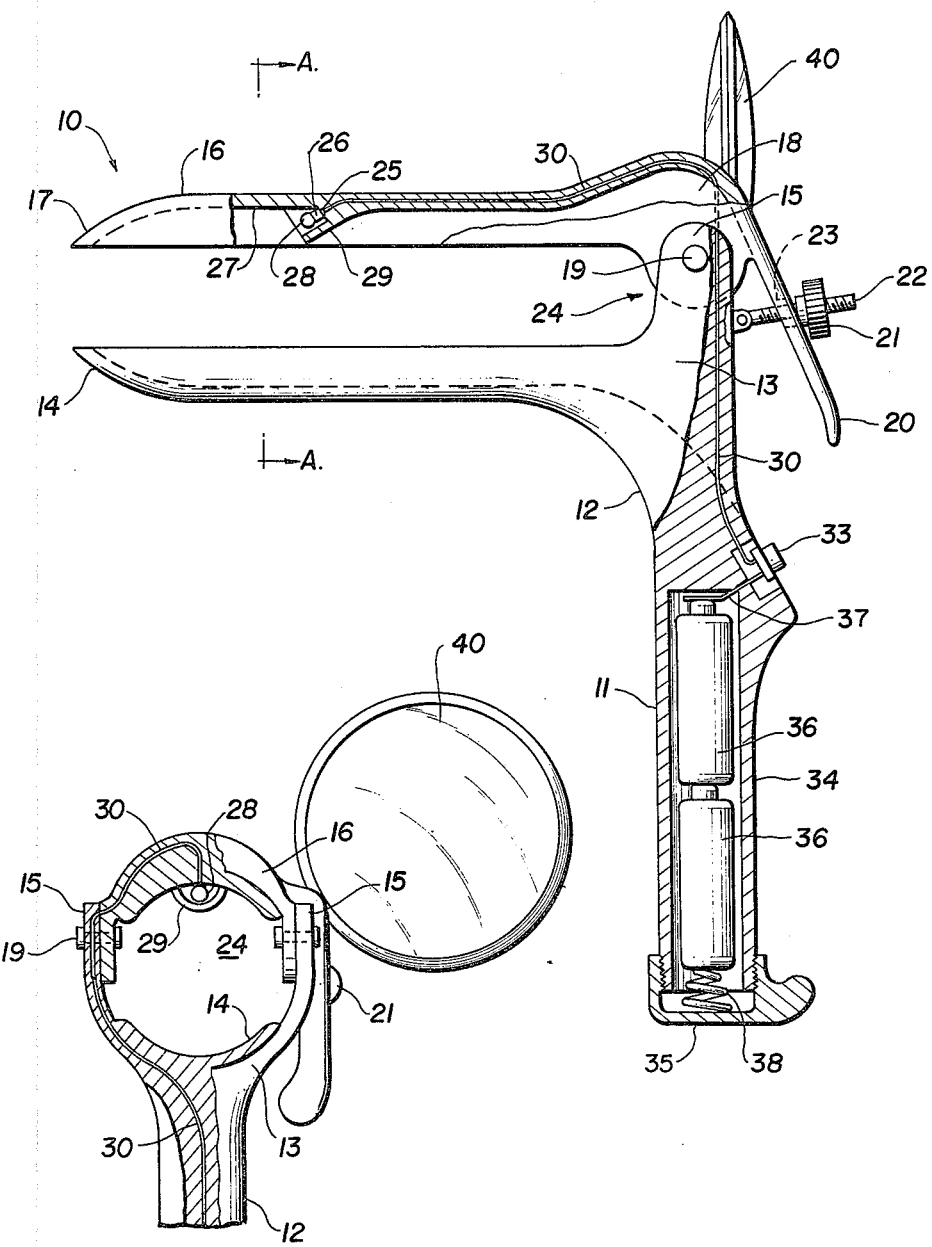
FIG. 1 is a side elevation view, partly in section, of an illuminated speculum according to the invention.
FIG. 2 is a view taken along line A—A of FIG. 1.

With reference to the drawings, a speculum 10 according to the present invention comprises a handle 11, a shank portion 12, a yoke portion 13 and a fixed lower blade 14, the handle 11, shank portion 12, yoke portion 13 and a lower blade 14 being preferably integrally formed as illustrated. As shown in FIG. 2, the yoke portion 13 is generally "U"-shaped and terminates in two opposedly spaced upwardly extending ears or lugs 15. An upper blade 16 having a distal tip portion 17 and a rear portion 18 is pivotally mounted between the lugs 15 of yoke 13 by means of pins 19. Affixed to the rear portion 18 of upper blade 16 is a rearwardly and downwardly extending lever 20.

Downward pressure on the lever 20 causes the blade 16 to pivot about pins 19 whereby the tip portion 17 of blade 16 is caused to move vertically with respect to the fixed lower blade 14. After the blade portions 14 and 16 have been inserted in the body orifice, the relative positions of the blades are adjusted by downward pressure on the lever 20 until the cavity is sufficiently enlarged for examination purposes. Further vertically upward movement of the upper blade 16 is restrained by tightening the threaded adjustment nut 21 on the threaded screw 22, one end of which is affixed to a lug 15 and which projects rearwardly through a slot 23 formed in the lever 20. A clear view of the interior of the cavity is obtained by sighting through the opening 24 in the direction of the tip 17 of upper blade 16. Thus far, what has been described is, generally speaking, a conventional vaginal speculum well-known to the obstetrical and gynecological medical arts.

Centrally mounted on the under surface 27 of upper blade 16 and between ¼ and 2/5 of the blade distance from the tip 17, preferably ⅓ of the distance, is a light fixture 25. This fixture 25 comprises a slightly downwardly projecting socket 26 embedded in the surface 27, and an incandescent or halogen bulb 28 recessed therebetween, i.e., the socket is flared in the downwardly projecting direction to serve as a shade 29 for the bulb; this structure minimizes light scattering and serves to direct as much light as possible to the interior of the cavity being examined. The shade 29 also screens the bulb from the observer's eye, and eliminates distressing glare.

Insulated, electrically conductive wire 30 is completely enclosed within a channel or the like formed in the blade 16 and is carried rearwardly and downwardly through a channel or the like formed in one of the lug portions 15 and shank portion 12 and terminates in electrical contact switch 33 located in the upper dorsal portion of handle 11. It will, of course, be understood that rather than providing wire conduit channels, the blade portion, lugs and associated shank portion may be of hollow construction thus providing a path for the wire 30.

Handle portion 11 is of hollow construction and is provided with a battery 34 and a removable cap portion 35 threadably engaged with the handle for removal and insertion of dry-cell batteries 36. The batteries are in electrical connection via contacts 37 and 38 in a conventional manner. It is, of course, to be realized that other types of batteries, such as for example, mercury cells, silver oxide cells or the like may also be employed.

To improve vision there is desirably provided a suitable magnifying lens 40 pivotable about an axis parallel to the opening 24 between the blades, and rotatable about its pivot axis so as to be capable of swinging from the position shown in FIG. 2 to a position axially aligned with the opening 24.

The hereinabove described instrument is an improvement over conventional illuminated specula, as the construction permits clear, unobstructed viewing of interior body cavities heretofore not possible with prior art instruments. It will be further noted that means for providing vertically upward adjustment of the upper blade has not been described as the provision of such means is well-known. It has, moreover, been determined that this conventional feature may, if desired, be eliminated as it is seldom used, thus resulting in a construction that is more simple and easier to manufacture and which is more adaptable to fabrication from a variety of materials such as plastics and the like in addition to conventional steel construction.

With reference to FIG. 3, a retractor 100 according to the present invention comprises a generally horizontally extending blade portion 111, a generally vertically downwardly depending shank portion 112 and a handle 113 disposed generally parallel to the blade portion 111, the blade 111, shank 112 and handle 113 being preferably integrally formed as illustrated. Preferably the blade 111 and the handle 113 are substantially parallel, with the shank portion 112 being disposed generally perpendicular thereto.

Mounted on the concave upper surface 114 of the blade 111 and ¼ to 2/5 of its length from the distal end 115 thereof, is a light fixture 116 comprising a slightly upwardly projecting socket 117 imbedded in the surface 114 and an incandescent or halogen bulb 118. The socket is flared in the direction of the distal end 115 of the blade 117 to serve as a shade 119 for the bulb to minimize light scattering and maximize the amount of light directed in the interior of the body cavity. The shade 119 also screens the bulb from the observer's eye and eliminates distracting glare.

An insulated electrically conductive wire 120 is enclosed within a channel or the like formed in the blade 111 and is carried rearwardly and downwardly through a channel or the like formed in the shank portion 112 and terminates in electrical contact switch 121 located in the upper portion of handle 113. It will, of course, be realized that rather than providing wire conduit channels, the blade portion and shank portion may be of hollow construction, thus providing a path for wire 120.

Handle portion 113 is of hollow construction and is provided with a battery case 122 and a removable cap portion 123 threadably engaged with the handle for removal and insertion of dry-cell batteries 124. The batteries are in electrical connection via contacts 125 and 126 in conventional manner. It is, of course, to be realized that other types of batteries, such as, for example, mercury or silver oxide cells or the like may be employed.

The hereinabove described instrument constitutes an advance and advantage over known instruments due to both the unique handle configuration of the retractor and the placement of the illuminating means, which facilitate manipulation of the retractor or speculum as well as permiting a clear, unobstructed, well-lit view of the interior of a body cavity. The presence, location and orientation of the light shield or shade 26, 116 is important to insure that the field of vision of the physician is unobscured by discharge from the body cavity. For use in a gynecological examination, for example, the bulb and the shade, properly oriented, provide a circular illuminated area on the entire vaginal fundus so that the center of the beam falls on the outlet of the cervical canal.

Although the invention has been described in considerable detail, in certain embodiments, such a description is intended solely for purposes of illustration and many variations therein may be made by those skilled in the art without departing from the spirit and scope of the invention.

What is claimed is:

1. A surgical retractor comprising:
   (a) a substantially straight, generally horizontally extending blade portion having a distal tip, a proximate end and a concave upper surface;
   (b) a shank portion generally downwardly vertically depending from the proximate end of said blade;
   (c) a handle portion joined to the lower end of said shank portion and projecting rearwardly therefrom and generally parallel to said blade portion;
   (d) illumination means for projecting a circle of light toward the tip of said blade, said means being mounted on the concave upper surface of said blade at a location between $\frac{1}{4}$ and 2/5 of the length of said blade from the tip thereof, said illumination means comprising a bulb and socket, said socket being formed in said concave surface and projecting slightly upwardly away from said blade at said location and in the direction of the tip of said blade;
   (e) said bulb being located externally of said blade;
   (f) said socket comprising a flared upper wall extending towards said tip to form an integral shade, whereby said socket and shade are integrally formed in said blade and whereby the user's eye is shielded from the direct light from said bulb, and whereby said shade also directs more of the light towards said tip to better illuminate the area under examination;
   (g) battery means contained in a hollow formed in said handle;
   (h) electrically conducting means connecting said illuminating means to said battery means; and
   (i) switch means for completing or interrupting the electrical circuit between said light fixture and said battery means.

2. The retractor of claim 1 wherein the blade portion, shank portion and handle portion are of integral construction.

3. The retractor of claim 1 wherein said electrically conducting means comprises insulated electrically conductive wire.

4. The retractor of claim 1 wherein said handle is provided with a removable cap portion to facilitate insertion and removal of the battery means.

* * * * *